(12) United States Patent
Abdul-Khalek

(10) Patent No.: US 6,796,165 B2
(45) Date of Patent: Sep. 28, 2004

(54) APPARATUS AND METHOD FOR REAL-TIME MEASUREMENT OF MASS, SIZE AND NUMBER OF SOLID PARTICLES OF PARTICULATE MATTER IN ENGINE EXHAUST

(75) Inventor: Imad Said Abdul-Khalek, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 10/620,063

(22) Filed: Jul. 15, 2003

(65) Prior Publication Data

US 2004/0139785 A1 Jul. 22, 2004

Related U.S. Application Data

(60) Provisional application No. 60/427,114, filed on Nov. 18, 2002.

(51) Int. Cl.[7] .................. G01N 15/02; G01N 15/06; G01M 15/00
(52) U.S. Cl. ............... 73/28.01; 73/23.33; 73/28.04; 73/118.1
(58) Field of Search .................... 73/23.33, 28.01, 73/28.04, 61.71, 61.72, 61.73, 116, 118.1, 117.2, 118, 863.11, 663.12, 863.21, 863.23

(56) References Cited

U.S. PATENT DOCUMENTS

| | | | |
|---|---|---|---|
| 3,986,386 A | 10/1976 | Beltzer et al. | |
| 4,586,367 A | 5/1986 | Lewis | 73/23.33 |
| 4,633,706 A | 1/1987 | Ito et al. | 73/23.33 |
| 5,546,788 A | 8/1996 | Dickow | |
| 6,148,656 A | 11/2000 | Breton | |
| 6,205,842 B1 * | 3/2001 | Patashnick et al. | 73/28.01 |
| 6,502,450 B1 * | 1/2003 | Patashnick et al. | 73/23.21 |
| 6,516,654 B2 * | 2/2003 | Uchihara et al. | 73/28.04 |

* cited by examiner

*Primary Examiner*—Daniel S. Larkin
(74) *Attorney, Agent, or Firm*—Gunn & Lee, P.C.

(57) ABSTRACT

An apparatus for real-time measurement of mass, size and number of solid particles of particulate matter in engine exhaust has a catalytic stripper to remove at least about 90% of a volatile fraction of the particulate matter and pass at least about 95% of a solid fraction of the particulate matter, and a micro-dilution tunnel to cool the test medium after passing through the catalytic stripper and prior to passing through a particle sizer and counter system. A method embodying the present invention includes removing a volatile fraction of the particulate matter carried in a sample test stream and comparing the sample after removal of the volatile fraction with a second sample in which the volatile fraction has not been removed. The difference between the two samples represents liquid phase of the volatile fraction of the tested exhaust gas.

13 Claims, 2 Drawing Sheets

APPARATUS AND METHOD FOR REAL-TIME MEASUREMENT OF MASS, SIZE AND NUMBER OF SOLID PARTICLES OF PARTICULATE MATTER IN ENGINE EXHAUST

This is a nonprovisional application claiming priority to U.S. Provisional Application Ser. No. 60/427,114 filed Nov. 18, 2002.

BACKGROUND OF THE INVENTION

1. Technical Field

This invention relates generally to an apparatus and method for determining the amount of solid particles of particulate matter in exhaust gas discharged from an internal combustion engine, and more particularly, to such an apparatus and method for measuring the mass, size and number of particles comprising solid and volatile particulate matter emitted from combustion sources in real-time.

2. Background Art

Particulate matter (PM) emitted from combustion sources, particularly diesel engines, is typically composed of volatile and solid fractions. The solid fraction, often referred to as "soot", consists mainly of carbon and a small amount of inorganic ash. The volatile fraction consists of unburned and partially burned fuel and lubricating oil, and sulfur compounds. Dry soot particles are formed in the combustion chamber of an engine while most of the volatile fraction enters the particle phase from the gas phase as the exhaust cools. The particle phase of the volatile fraction consists of precipitated liquid particles and precipitated liquid that attach to preexisting solid particles. Hence, particulate matter is a combined measure of solid and volatile fractions. It is important to be able to distinguish between the two components because the mechanism of their formation and control are different.

Several systems and methods have been proposed for the measurement of total (solid and precipitated volatile fractions) particulate mass. For example, U.S. Pat. No. 6,148,656, granted to Leo Breton on Nov. 21, 2000, for a REAL-TIME ON-ROAD VEHICLE EXHAUST GAS MODULAR FLOW METER AND EMISSIONS REPORTING SYSTEM, describes an on-road system for measuring emissions from a vehicle in real-time. The system provides a chemical analysis and measure of total particulate matter emitted, which can be expressed in grams per mile. However, this system is not capable of identifying the solid particles separately attributable to the solid and volatile fractions of the particulate material, nor in identifying the size distribution and number of solid particles.

The measurement and identity of the solid and volatile fractions of particulate matter in real-time would be of great value to engine developers and emission researchers focusing on ways to characterize and reduce soot emissions. Furthermore, if the solid particle measurement is conducted with the volatile fraction removed, in parallel with a measurement of total particulate matter (soot and volatile fractions), one would also be able to determine volatile PM emissions in real-time, by taking the difference between the solid PM and total PM. Currently, no available method is capable of facilitating the measurement of solid particle mass, number and size emissions in real-time. Most available methods rely on chemical work-up, and they are slow, notwithstanding the elaborate system proposed by Breton as discussed above, and often take several hours to several days from the time of initial measurement. Aside from particle mass, the results from available methods are not capable of establishing particle number and size.

The present invention is directed to overcoming the problem of separately identifying the source of particulate matter in emissions attributable to the solid and the volatile fractions of the particulate matter. It is desirable to have an apparatus and method that can remove the volatile fraction from the particulate matter, leaving only particles from the solid fraction for measurement of mass, size distribution and number. It is also desirable to have such an apparatus and method that can provide rapid cooling prior to the measurement of solid particles to inhibit the formation of sulfuric acid particles during cool down from a higher exhaust temperature.

SUMMARY OF THE INVENTION

In accordance with one aspect of the present invention, a method for real-time measurement of the mass, size and number of solid fraction particulate matter in exhaust gas discharged from an internal combustion engine includes discharging exhaust gas from the engine over a predefined period of time while operating the engine in a predetermined mode. A first sample of the discharged exhaust gas is continuously collected throughout the predefined period of time and passed through a catalytic stripper that removes at least about 90% of the volatile fraction from the first gas sample. The first sample is then cooled to a temperature less than about 52° C. and the size and number of solid particles contained in the first sample of exhaust gas are measured over the predefined period of time. The measured size and number of solid particles are representative of the distribution of the solid fraction particulate matter discharged from the engine over the predefined period of time. The solid particles are collected over the predefined period of time and the mass of the collected solid particles measured. The measured mass of solid particles contained in the first sample is representative of the total mass of the solid fraction of the particulate matter discharged from the engine over the predefined period of time.

Other aspects of the method embodying the present invention include continuously collecting a second sample of the exhaust gas discharged from the internal combustion engine over a like predefined period of time, and cooled to a temperature sufficient to precipitate substantially all of the volatile fraction from the gaseous phase to a liquid phase. The solid fraction of the particulate matter and the precipitated liquid phase of the volatile fraction formed throughout the like period of time are collected and measured. The measured mass is representative of the total mass of the solid fraction and the liquid particles of the volatile fraction comprising the particulate matter discharged from the engine during the like period of time.

Another aspect of the method embodying the present invention includes calculating the difference between the mass of the first and second samples of exhaust gas, the difference being representative of the volatile fraction particulate matter contained in the exhaust gas discharged from the engine.

In accordance with another aspect of the present invention, an apparatus for real-time measurement of the mass, size and number of solid fraction and volatile fraction particulate matter in exhaust gas discharged from an internal combustion engine includes a catalytic stripper in fluid communication with an exhaust system of the engine. The catalytic stripper is adapted to remove at least about 90% of the volatile fraction particulate matter from the exhaust gas and pass at least about 95% of the solid fraction particulate matter of the exhaust gas. The apparatus further includes a micro-dilution tunnel in fluid communication with the catalytic stripper. The micro-dilution tunnel is adapted to mix air having a temperature of less than that of the exhaust gas with the exhaust gas and form a mixture of air and exhaust gas having a temperature of less than 52° C. The apparatus further includes a particle sizer and a particle counter in fluid communication with the micro-dilution tunnel. A means for continuously collecting particulate matter contained in the mixture of air and exhaust gas over a predefined period of time is also provided, along with a means for measuring the total mass of the particulate matter collected over the predefined period of time.

Other aspects of the apparatus embodying the present invention include a dilution tunnel interposed between the exhaust system of the engine and the catalytic stripper. The dilution tunnel is adapted to mix air with the exhaust gas discharged from the engine and provide a mixture of air and exhaust gas to the catalytic stripper.

BRIEF DESCRIPTION OF THE DRAWINGS

A more complete understanding of the structure and operation of the present invention may be had by reference to the following detailed description when taken in conjunction with the accompanying drawings, wherein.

DETAILED DESCRIPTION OF THE INVENTION

Figure 1:
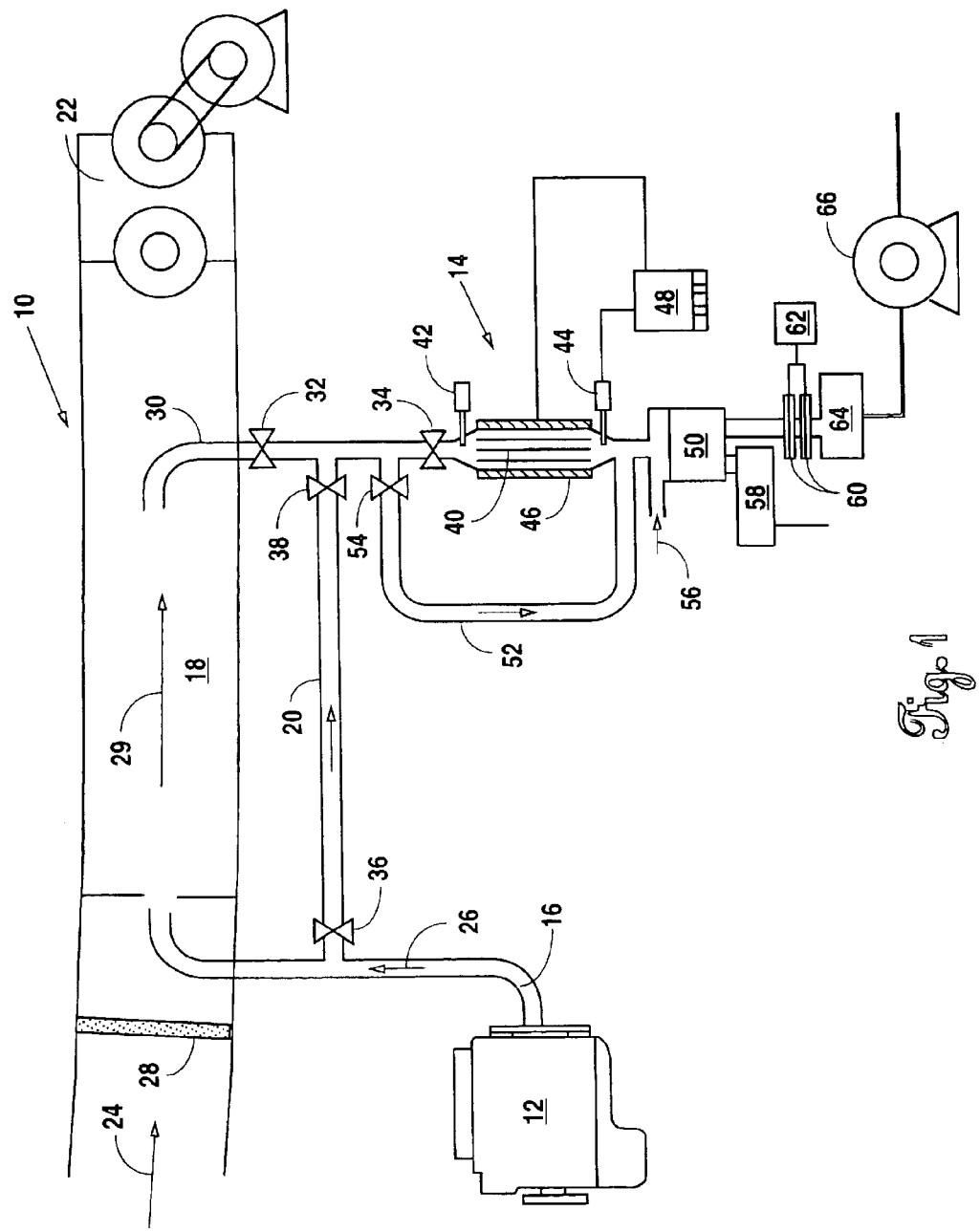
FIG. 1 is a schematic diagram of an apparatus, embodying the present invention, for the measurement, in real-time, of mass, size and number of solid and volatile particulate matter in the exhaust gas discharged from an internal combustion engine.

In a preferred embodiment of the present invention, an apparatus for the measurement, in real-time of the mass, size and number of solid and volatile particulate matter in the exhaust gas discharged from an internal combustion engine 12 is generally indicated by the reference numeral 10 in FIG. 1. The apparatus 10 includes a catalytic stripper system 14 disposed in fluid communication with an exhaust system 16 of the engine 12, either by way of a full flow dilution tunnel 18 or a conduit 20 extending between the exhaust system 16 and the catalytic stripper system 14.

In the preferred embodiment, the dilution tunnel 18 is a conventional dilution device used to dilute exhaust gas emitted from an engine with air, and thereby provide a relatively low temperature mixture of air and exhaust gas that is beneficial for analyzing and measuring exhaust gas content. The dilution tunnel 18 has a HEPA filter 28 disposed at an end through which fresh air, represented by the arrow 24, is drawn, and a blower and heat exchanger unit 22 disposed at an opposite end of the tunnel 18. The exhaust system 16 of the engine 12 is in communication with the dilution tunnel 18 whereby exhaust gas, represented by the arrow 26, is introduced into the dilution tunnel 18 and mixed with air to form a mixture of exhaust gas and air, as indicated by the arrow 29.

A representative sample of the diluted exhaust gas 29 is drawn from the dilution tunnel 18 and into a sampling tube 30 by an air pump 66 disposed at a downstream end of the apparatus 10. As illustrated schematically in FIG. 1, the sampling tube 30 extends between the dilution tunnel 18 and the catalytic stripper system 14. The sampling tube 30 provides direct communication between the dilution tunnel 18 and the catalytic stripper system 14 when a first flow control valve 32, disposed in the sampling tube 30 at a position between the dilution tunnel and a connection between the conduit 20 and the sampling tube, is open and a second flow control valve 34 disposed in the sampling tube 30 at a position between the connection of the conduit 20 with the sampling tube and the catalytic stripper system 14, is also in an open position. A direct undiluted flow of exhaust gas can be delivered to the catalytic stripper system 14 by closing the first flow control valve 32, opening a third flow control valve 36 disposed in the conduit 20 at a position adjacent a connection of the conduit 20 with the exhaust system 16, and opening a fourth flow control valve 38 disposed in the conduit 20 at a position adjacent a connection of the conduit 20 with the sampling tube 30. Thus, diluted exhaust gas 29 can be provided to the catalytic stripper system 14 by closing the third and fourth flow control valves 36, 38, and opening the first and second flow control valves 32, 34. In a similar manner, undiluted exhaust gas 26 can be delivered directly from the exhaust system 16 of the engine 12 to the catalytic stripper system 14 by closing the first flow control valve 32, and opening the third and fourth flow control valves 36, 38.

In the preferred embodiment of the present invention, the catalytic stripper system 14 has a conventional oxidation catalyst 40, such as a diesel oxidation catalyst having a platinum-loaded honeycomb structure. The flow-thru catalyst substrate is designed to provide enough residence time for unburned and partially burned fuel and lube oil molecules to diffuse to the internal surface of the substrate channels and become oxidized. Importantly, the catalyst 40 strips hydrocarbon (HC) molecules from the sample through conversion of HC to carbon dioxide ($CO_2$) and water ($H_2O$).

Other components of the catalytic stripper system 14 include a first temperature sensor 42 disposed in the sampling tube 30 at a position adjacent an inlet end of the catalyst 40, and a second temperature sensor 44 disposed at an outlet end of the catalyst 40. The catalytic stripper system 14 also includes a heater 46, such as a resistance cartridge heater, disposed in intimate contact with the catalyst 40 to heat the catalyst to a selected temperature. A temperature controller 48 is in electrical communication with at least one of the temperature sensors 42, 48 and with the heater 46. The heater 46 and the temperature controller 48 controllably heats and maintains the catalyst 40 at a temperature within a range of from about 250° C. to about 500° C., and preferably about 350° C., to oxidize the volatile fraction of the particulate matter.

A bypass conduit 52 is provided to direct fluid flow around the catalyst 40 when it is desired to measure a sample containing both solid and volatile fractions of particulate matter. Flow around the catalyst 40 is controlled by a fifth flow control valve 54 positioned in the bypass conduit 52 at a position adjacent a connection of the bypass conduit 52 with the sampling tube 30. When bypassing the catalyst 40, it may also be desirable to have an additional flow control valve, not shown, of the discharge end of the catalyst 40 to prevent back flow into the catalyst.

The catalytic stripper system 14 also includes a micro-dilution tunnel 50 adapted to provide clean compressed air, indicated by the arrow 56, to quickly (i.e., in less than about 100 ms) cool the diluted exhaust gas 29 or undiluted raw exhaust 26 samples, as required and explained below in greater detail.

The apparatus 10 also includes a particle detection sizer and counter system 58 that is adapted to analyze a representative portion, e.g., 10%, of the total sample under test. The particle detection sizer and counter system 58 includes a conventional sizer, such as the Scanning Mobility Particle Sizer Model No. 3934 manufactured by TSI, and a conventional particle counter, such as the Condensation Particle Counter Model No. 3025 also manufactured by TSI. The particle detection sizer and counter system 58 provides for a controlled predetermined volumetric flow of the mixture of air and exhaust gas through the system, and requires that the temperature of the test sample passing through be substantially at ambient temperature, i.e., about 25° C. The particle detection sizer and counter system 58 is able to determine the size of particles, the size distribution of particles, and the number of particles passing through the system 58. The size, distribution and number of particles is representative of the total sample.

The apparatus 10 also includes a means for continuously collecting particulate matter contained in the remaining portion of the air and exhaust gas mixture over a predefined period of time, e.g., a 20 minute cycle, such as a filter pack 60 positioned at an outlet end of the micro-dilution tunnel 50. The apparatus 10 also includes a means 62, for example, an analytical balance scale, for measuring the total mass of particulate matter collected over the predefined period of time.

In the preferred embodiment of the present invention, the apparatus 10 includes a means 64 for measuring the mass flow, for example a conventional mass flow sensor, of the mixture of air and exhaust gas from which solid particles have been removed by the filter pack 60 over the predefined period of time, is desirably positioned downstream of the filter pack 60.

Figure 2:
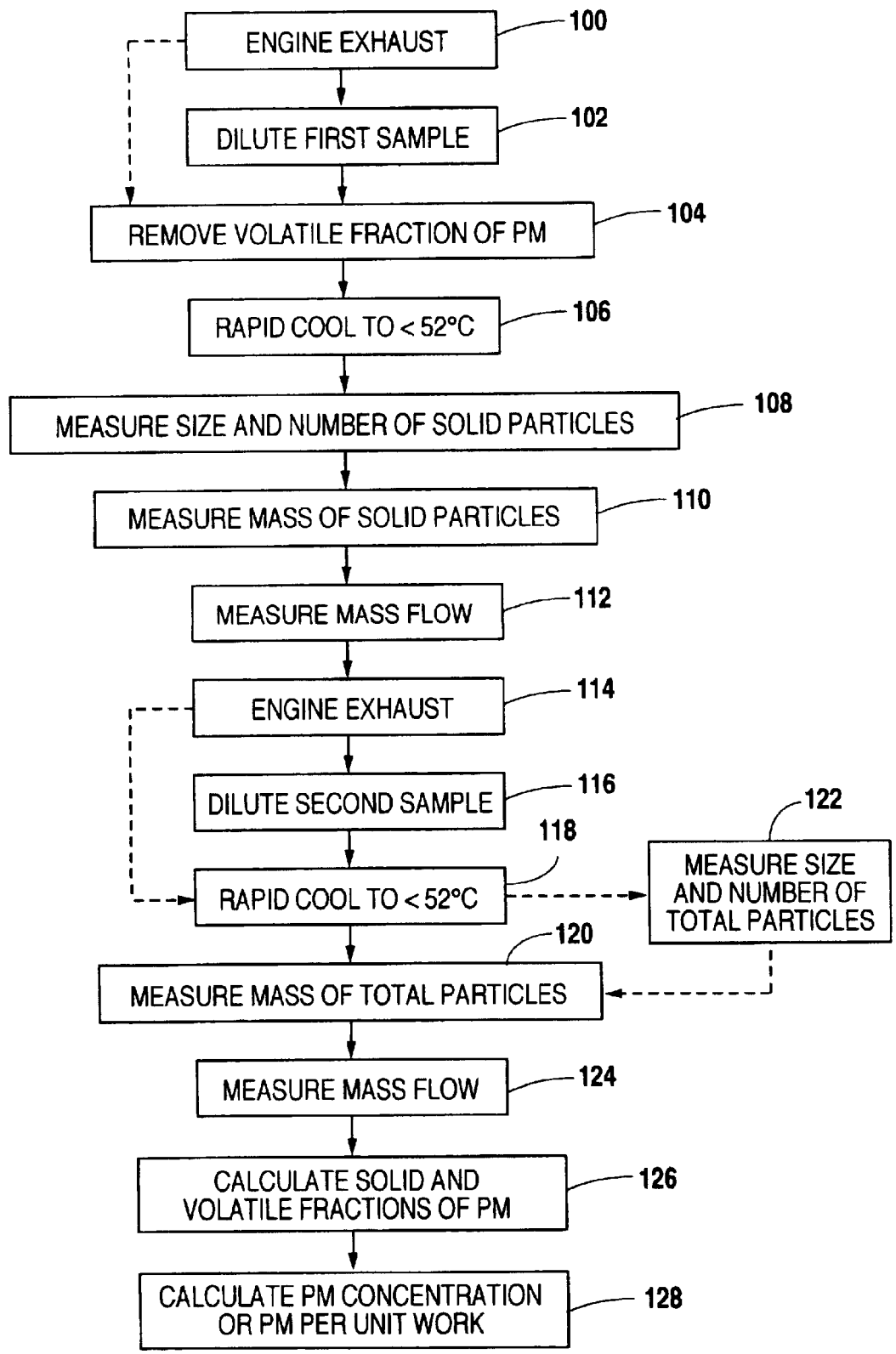
FIG. 2 is a flowchart illustrating a method, embodying the present invention, for the real-time measurement of the mass, size and number of solid and volatile particulate matter in exhaust gas.

The method for measuring, in real-time, the mass, size and number of particulate matter in exhaust gas discharged from an internal combustion engine in accordance with the present invention, is illustrated by the flowchart shown in FIG. 2. Engine exhaust, as represented at block 100, is delivered to the dilution tunnel 18 by way of exhaust system 16 of the engine 12 and diluted, as indicated at block 102, to provide a first sample for testing. The first sample, representative of the mixture of air and exhaust gas flowing through the dilution tunnel, is withdrawn from the dilution tunnel by the pump 66. Alternatively, the engine exhaust gas 16 may be routed directly, without dilution, to the catalytic stripper system 14 by way of the conduit 20, as described above. The withdrawn first sample is passed through the catalytic stripper system 14 whereupon at least 90% of the volatile fraction of particulate matter is removed from the stream of air and exhaust gas, as indicated at block 104. The catalytic stripper system 14 is designed to allow more than 95% passage of the solid fraction particulate matter, while removing more than 90% of volatile hydrocarbon and sulfate materials that are typically present in engine exhaust.

After passing through the catalytic stripper system 14, the first test sample flows through the micro-dilution tunnel 50. The micro-dilution tunnel 50 adds clean compressed air 56, and quickly (in less than 100 ms), further dilutes the heated mixture of air and exhaust gas, or the raw exhaust sample, to bring the sample to a temperature of less than 52° C. and preferably about 25° C., as indicated at block 106. Rapid cooling inhibits the formation of sulfuric acid particles and reduces the thermophoretic deposition of particles on walls of the several components of the catalytic stripper system 14.

A predetermined volumetric portion of cooled first test sample is directed through the particle detection size and counter system 58 whereat the size and number of solid particles are measured as indicated at block 108. The mass of the solid particles in the remaining portion of the first test sample collected on the filter pack 60 during the length of time over which the test is conducted, e.g., a 20 minute cycle, is measured as represented at block 110, and the mass flow of the remaining portion of the test stream measured as represented at block 112.

A second sample of exhaust gas 26, as indicated at block 114, is directed to the dilution tunnel whereupon it is diluted with air 24 as indicated at block 116. Alternatively, if it is desired that the second sample be undiluted exhaust gas, the engine exhaust gas may be directed around the dilution tunnel 18 by the conduit 20, as described above.

In the illustrated embodiment described herein, the second sample bypasses the catalytic stripper system 14 and is routed directly to the micro-dilution tunnel 50 whereupon the second test sample is cooled as represented at block 118.

Total particulate matter, i.e., solid fraction and precipitated volatile fraction particles carried in the second sample are collected on the filter pack 60 and measured as indicated at block 120. For collection purposes, it is only necessary to rapidly cool the second sample to a temperature less than about 52° C. However, if it is desired to measure the size and number of total particles of the second stream, as indicated by block 122 connected by dotted lines between blocks 118 and 120 by passing a portion of the second sample through the particle detection sizer and counter system 58, it is necessary that the test sample be cooled to a temperature near ambient, i.e., about 25° C.

The mass flow of the second sample, after removal of the total particulate matter, is measured as indicated at block 124.

The respective solid and volatile fractions of particulate matter carried in the exhaust stream is then calculated as represented by block 126. The first and second test samples should be conducted in parallel with the same exhaust gas flow and carried out over equal amounts of time. The total particulate matter (the solid fraction and the liquid phase particles of the volatile fraction) is represented by the measurements of the total particulate matter of the second sample. In the first sample, substantially all of the volatile fraction is removed by the catalytic stripper system so that only particulate matter comprising the solid fraction are collected and measured. Therefore, the volatile fraction of the particulate matter is identified by subtracting the measured mass of particulate matter of the first sample from the measured mass of the total particulate matter of the second sample. Furthermore, the size, size distribution and number of particles carried in the first test stream, and if desired in the second test stream, may be readily provided in real-time by readouts on the particle detection sizer and control system 58.

Particulate matter is sometimes expressed as the concentration of PM in the exhaust stream, e.g., in parts per cubic centimeter. The concentration of particulate matter in the exhaust stream can be obtained using the method embodying the present invention. If suitable flow sensors are placed in the exhaust system 16 of the engine 12 and in the dilution tunnel 18, the dilution ratio, if any, of exhaust gas 26 introduced into the sampling tube 30 can be readily ascertained. Further, the mass flow sensor 64 disposed downstream of the filter pack 60 measures mass flow after dilution by air introduced into the micro-dilution tunnel 50. Therefore, the amount of the exhaust gas 26 contained within the respective first and second samples as the samples respectively pass through the particle detection sizer and counter system 58 and the filter pack 60 can be readily determined, and the concentration of solid particulate matter in the exhaust gas stream determined, as indicated at block 128. If it is desirable to define the particulate matter carried in the exhaust stream per unit of distance, e.g., grams per mile (g/mi) or grams per horsepower hour (g/Hph), the vehicle distance traveled, or the horsepower produced by the engine 12 during the test cycle can be multiplied by the time of the test cycle, and the mass of the collected particulate matter divided by the distance traveled or by the product of horsepower and time.

Although the present invention is described in terms of preferred illustrative embodiments, those skilled in the art will recognize that the above-described apparatus and method are illustrative of a typical arrangement for using the apparatus and method embodying the present invention. For example, the two-way flow control valves could be substituted for a fewer number of three-way flow control valves. In a similar manner, the steps described for treating and testing the first test sample could just as easily be carried out after the steps described for treating the second sample. That is, the order in which the test samples are taken and tested is inconsequential in carrying out the method embodying the present invention. Such arrangement of the apparatus and application of the method embodying the present invention are intended to fall within the scope of the following claims.

Other aspects, features, and advantages of the present invention may be obtained from a study of this disclosure and the drawings, along with the appended claims.

What is claimed is:

1. A method for real-time measurement of the mass, size and number of particles defining particulate matter in exhaust gas discharged from an internal combustion engine, comprising:
    discharging exhaust gas from the internal combustion engine over a predefined period of time while operating in a predetermined mode, the particulate matter contained in the discharged exhaust gas having a volatile fraction disposed primarily in a gaseous phase comprising unburned and partially burned fuel and lubricating oil, and sulfur compounds, and a solid fraction comprising particles of carbon and inorganic ash;
    continuously collecting a first sample of the discharged exhaust gas throughout the predefined period of time;
    directing the first sample of the exhaust gas through a catalytic stripper and removing at least about 90% of the volatile fraction from the first sample and passing at least about 95% of the solid fraction of the first sample through the catalytic stripper;
    cooling the first sample of exhaust gas to a temperature of from about 25° C. to about 52° C.;
    measuring the size and number of particulate matter contained in a representative portion of the cooled first sample of exhaust gas over the predefined period of time, the measured size and number of particulate matter being representative of the distribution of particles defining the solid fraction of the particulate matter discharged from said engine over the predefined period of time;
    collecting the particulate matter from the first sample of exhaust gas over the predefined period of time; and
    measuring the mass of the collected particulate matter of the first sample, said measured mass being representative of the total mass of the solid fraction particulate matter discharged from said engine over the predefined period of time.

2. The method as set forth in claim 1, wherein said method includes:
    discharging exhaust gas from the internal combustion engine while operating in said predetermined mode over a predefined period of time comparable to the predefined period of time during which the first sample was collected;
    continuously collecting a second sample of the exhaust gas throughout the comparable period of time;
    cooling the second sample of the exhaust gas to a temperature sufficient to precipitate substantially all of the volatile fraction from said gaseous phase to a liquid phase;
    collecting the solid fraction and the precipitated liquid phase particles of the volatile fraction formed throughout the comparable period of time; and
    measuring the total mass of the collected solid fraction and the precipitated liquid phase of the volatile fraction, said measured mass being representative of the total particulate matter discharged from said engine during said comparable period of time.

3. The method as set forth in claim 2, wherein said method includes:
    calculating the difference between the mass of said first and second samples of exhaust gas, said difference being representative of the volatile fraction particulate matter contained in the exhaust gas discharged from said engine.

4. The method as set forth in claim 2, wherein said method includes passing the discharged exhaust gas through a dilution tunnel and mixing the exhaust gas with air having a defined mass flow rate before continuously collecting the first and second samples.

5. The method as set forth in claim 2, wherein cooling the first and second samples includes mixing the samples with air in a micro-dilution tunnel.

6. The method as set forth in claim 5, wherein said collecting the solid particles of the first sample, and collecting the particles of the solid fraction and the precipitated liquid phase of the volatile fraction of the second sample, includes collecting the particles of the solid fraction and the precipitated liquid phase of the volatile fraction on a filter disposed downstream of the micro-dilution tunnel wherein said samples are cooled.

7. The method, as set forth in claim 2, wherein cooling the first and second samples includes rapidly cooling the samples at a rate sufficient to impede the formation of sulfuric acid particles.

8. The method, as set forth in claim 1, wherein measuring the size and number of particulate matter contained in a representative portion of the cooled first sample of exhaust gas over the predefined period of time includes passing the representative portion through a particle sizer adapted to determine the size of particulate matter in the representative portion of the first sample, and a particle counter adapted to measure the total number of particulate matter in the representative portion passing through the counter over said predefined time period.

9. The method, as set forth in claim 1, wherein said method includes heating the catalytic stripper to a preselected temperature having a range of from about 250° C. to about 500° C., and maintaining the catalytic stripper at said preselected temperature while passing the first sample of exhaust gas through the catalytic stripper.

10. An apparatus for real-time measurement of the mass, size and number of particles defining particulate matter in exhaust gas discharged from an internal combustion engine, comprising:

a catalytic stripper in fluid communication with an exhaust system of said engine and adapted to remove at least about 90% of a volatile fraction from the exhaust gas and pass at least 95% of a solid fraction of the exhaust gas through the catalytic stripper;

a micro-dilution tunnel in selective fluid communication with said catalytic stripper and adapted to mix air having a temperature less than that of the exhaust gas with the exhaust gas and form a mixture of air and exhaust gas having a temperature of less than about 52° C.;

a particle sizer in fluid communication with said micro-dilution tunnel;

a particle counter in fluid communication with said micro-dilution tunnel;

a means for continuously collecting particulate matter contained in the mixture of air and exhaust gas over a predefined period of time; and a means for measuring the mass of the particulate matter collected over said predefined period of time.

11. The apparatus as set forth in claim 10, wherein said apparatus includes a dilution tunnel interposed between an exhaust system of said engine and said catalytic stripper, said dilution tunnel being adapted to mix air with the exhaust gas discharged from said engine and provide a mixture of air and exhaust gas to said catalytic stripper.

12. The apparatus as set forth in claim 10, where said apparatus includes a means for controllably heating the catalytic stripper to a temperature having a range from about 250° C. to about 500° C.

13. The apparatus as set forth in claim 10, wherein said apparatus includes a means for measuring the mass flow of the mixture of air and exhaust gas from which the particulate has been collected by said means for continuously collecting particulate matter contained in the mixture of air and exhaust gas over a predefined period of time.

* * * * *